US011236355B2

United States Patent
Staskawicz et al.

(10) Patent No.: US 11,236,355 B2
(45) Date of Patent: Feb. 1, 2022

(54) ROQ1 PROVIDES RESISTANCE TO BOTH XANTHOMONAS AND PSEUDOMONAS IN PLANTS

(71) Applicant: The Regents of the University of California, Oakland, CA (US)

(72) Inventors: Brian J. Staskawicz, Berkeley, CA (US); Alexander Christiaan Schultink, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 16 days.

(21) Appl. No.: 16/639,379

(22) PCT Filed: Aug. 21, 2018

(86) PCT No.: PCT/US2018/047312
§ 371 (c)(1),
(2) Date: Feb. 14, 2020

(87) PCT Pub. No.: WO2019/040483
PCT Pub. Date: Feb. 28, 2019

(65) Prior Publication Data
US 2021/0130843 A1 May 6, 2021

Related U.S. Application Data

(60) Provisional application No. 62/548,913, filed on Aug. 22, 2017.

(51) Int. Cl.
*C12N 15/82* (2006.01)
*C07K 14/415* (2006.01)

(52) U.S. Cl.
CPC ........ *C12N 15/8281* (2013.01); *C07K 14/415* (2013.01)

(58) Field of Classification Search
CPC .......................... C12N 15/8281; C07K 14/415
See application file for complete search history.

(56) References Cited

U.S. PATENT DOCUMENTS

| 6,608,241 B1 * | 8/2003 | Beachy | A01H 1/00 435/252.2 |
| 2009/0138988 A1 | 5/2009 | Wang et al. | |
| 2013/0298265 A1 * | 11/2013 | Cunnac | C12N 15/10 800/13 |
| 2016/0032303 A1 | 2/2016 | Lahaye et al. | |

OTHER PUBLICATIONS

Piechocki et al (An Engineered Distant Homolog of Pseudomonas syringae TTSS Effector From Physcomitrella patens Can Act as a Bacterial Virulence Factor. Frontiers in Microbiology. 1-8, 2018) (Year: 2018).*
Thomas et al, (The Immune Receptor Roq1 Confers Resistance to the Bacterial Pathogens Xanthomonas, Pseudomonas syringae, and Ralstonia in Tomato. Frontiers in Microbiology. 1-10, 2020) (Year: 2020).*
Sierro et al (The tobacco genome sequence and its comparison with those of tomato and potato. Nature communications. 1-9, 2014) (Year: 2014).*
NCBI (XP_019226668, published Dec. 5, 2016) (Year: 2016).*
Teper et al (Xanthomonas euvesicatoria type III effector XopQ interacts with tomato and pepper 14-3-3 isoforms to suppress effector-triggered immunity. The Plant Journal 77, 297-309, 2014). (Year: 2014).*
Li et al. (The HopQ1 Effector's Nucleoside Hydrolase-Like Domain Is Required for Bacterial Virulence in *Arabidopsis* and Tomato, but Not Host Recognition in Tobacco. Plos One. 1-9, 2013). (Year: 2013).*
Zembek et al (Two Strategies of Pseudomonas syringae to Avoid Recognition of the HopQ1 Effector in Nicotiana Species. Frontiers in Plant Science. 1-9, 2018) (Year: 2018).*
Friedberg (Automated protein function prediction—the genomic challenge. Brief. Bioinformatics. 7:225-242, 2006) (Year: 2006).*
Adlung et al., "Dissecting virulence function from recognition: cell death suppression in Nicotiana benthamiana by XopQ/HopQ1-family effectors relies on EDS1-dependent immunity", The Plant Journal, 2017. 91: 430-442.
Powell et al., "Protection against tobacco mosaic virus in transgenic plants that express tobacco mosaic virus antisense RNA", Proc. Natl. Acad. Sci., Sep. 1989, 86: 6949-6952.
Schultink et al., "Roq1 mediates recognition of the Xanthomonas and Pseudomonas effector proteins XopQ and HopQ1", The Plant Journal, 2017, 92: 787-795.
UniProtKB—A0A1S3ZSF5 (A0A1S3ZSF5_TOBAC), TMV resistance protein N-like. UnitProtKB Accession No. A0A1S3ZSF5. Last Sequence Update: Apr. 12, 2017. [online]. [Retrieved on Oct. 2, 2018]. Retrieved from the Internet <URL: https://www.uniprot.org/uniprot/A0A1S3ZSF5> Protein; Organism; and Sequence.
Adlung et al., "Non-host Resistance Induced by the Xanthomonas Effector XopQ Is Widespread within the Genus *Nicotiana* and Functionally Depends on EDS1", Frontiers in Plant Science, Nov. 2016, 7: 1796.
Bentham et al., "Animal NLRs provide structural insights into plant NLR function", Annals of Botany, 2017, 119: 689-702.
Burk et al., "The Genus Nicotiana: A Source of Resistance to Diseases of Cultivated Tobacco", Econ Bot 20, 1966, 76-88. https://doi.org/10.1007/BF02861929.
Dijk et al., "Reactions of Nicotiana species to a potato viruses A, X and Y and tobacco mosaic virus in relation to their taxonomy and geographical origin", Neth. J. Pl., 1989, 95: 343-356.

(Continued)

*Primary Examiner* — Ashley K Buran
*Assistant Examiner* — Wayne Zhong
(74) *Attorney, Agent, or Firm* — James S. Keddie; Bozicevic, Field & Francis LLP

(57) ABSTRACT

Provided herein is a non-*Nicotiana* transgenic plant comprising an exogenous polynucleotide encoding *Nicotiana benthamiana* Roq1 or a variant thereof. These plants have enhanced resistance to at least one species of *Xanthomonas, Pseudomonas, Ralstonia*, and/or another pathogen containing a homolog of XopQ whose recognition is mediated by Roq1.

9 Claims, 11 Drawing Sheets
Specification includes a Sequence Listing.

(56) References Cited

OTHER PUBLICATIONS

Steinbrenner et al., "Effector Recognition and Activation of the *Arabidopsis thaliana* NLR Innate Immune Receptors", Cold Spring Harbor Symposia on Quantitative Biology, 2012, vol. LXXVII, pp. 249-257.

\* cited by examiner

ROQ1 PROVIDES RESISTANCE TO BOTH XANTHOMONAS AND PSEUDOMONAS IN PLANTS

CROSS-REFERENCING

This application is the national phase under 35 U.S.C. § 371 of International Application No. PCT/US2018/047312, filed on Aug. 21, 2018, which claims the benefit of U.S. provisional application Ser. No. 62/548,913, filed on Aug. 22, 2017, which applications are incorporated by reference in their entireties.

STATEMENT REGARDING FEDERALLY SPONSORED RESEARCH

This invention was made with government support under Grant No. 2016-67012-25106 awarded by the United States Department of Agriculture. The government has certain rights in the invention.

BACKGROUND

Plant pathogens are a significant problem for agriculture, resulting in an estimated 10% decrease in crop yields despite control measures (Oerke, 2005). Utilizing genetic resistance to protect plants is generally preferable over chemical methods, which can be more expensive and pose risks to human or environmental health (Jones et al., 2014; Vincelli, 2016); however in many cases genetic resistance is not available. The identification of the genetic basis of disease resistance pathways can allow for the creation of resistant crop varieties either through breeding or transgenic approaches (Dangl et al., 2013; Rodriguez-Moreno et al., 2017). As pathogens may evolve to overcome resistance mediated by a single resistance gene, it's desirable to utilize several independent resistance pathways against the same pathogen to confer durable resistance. The identification of resistance genes, particularly those that have broad specificity across many pathogen species, therefore remains a significant focus of plant pathology research.

Plant bacterial pathogens in the genus *Xanthomonas* contain a Type III Secretion System, which is used to deliver effector proteins into the plant cell (Rossier et al., 1999). These effector proteins can function to suppress the immune system of the plant or to manipulate the metabolism of the host to promote pathogenesis (Gürlebeck et al., 2006; Block et al., 2008; Toruño et al., 2016). While effector proteins are typically beneficial to the pathogen, if the plant contains a perception pathway capable of detecting a particular effector protein a strong immune response can be triggered, known as Effector Triggered Immunity (ETI) (Alfano and Collmer, 2004; Chisholm et al., 2006; Jones and Dangl, 2006). An ETI response is often associated with a visible cell death response known as the hypersensitive response. Identification of the genes responsible for specific ETI pathways can allow for engineering disease resistance into susceptible crop varieties.

Many ETI responses in plants are mediated by a member of the nucleotide-binding leucine-rich repeat (NLR) protein family, with the typical plant genome encoding between 100 and 600 of these proteins (Jones et al., 2016). The recognition of an effector protein by an NLR may be through a direct physical interaction or may involve additional protein components. NLR proteins can be divided into groups based on their domain architecture, as well as genetic dependencies required for their function. The two N-terminal domains common on plant NLR proteins are the Toll-like interleukin-1 receptor (TIR) domain on TIR-NLRs (TLRs) and the coiled coil domain on CC-NLRs. All NLR proteins appear to depend on the protein SGT1 for function, whereas the TLRs require a functional EDS1 protein and a subset of the CC-NLRs require the NRC proteins (Wiermer et al., 2005; Shirasu, 2009; Wu et al., 2016). These genetic dependencies can be used to help determine which family or clade of genes may be responsible for mediating the perception of a particular effector protein.

The effector protein XopQ from *Xanthomonas*, and the close-homolog HopQ1 from *Pseudomonas*, are widely distributed and highly conserved among various species in these genera. XopQ and HopQ1 have been shown to suppress the immune system of the plant and promote pathogen virulence (Li et al., 2013a; Sinha et al., 2013; Hann et al., 2014; Teper et al., 2014; Gupta et al., 2015). The mechanism by which XopQ/HopQ1 suppress immunity is not fully understood and is complicated by the observation that XopQ recognition in *N. benthamiana* can suppress visible cell death responses independently from the virulence activity of XopQ (Adlung and Bonas, 2017). The protein has homology to nucleoside hydrolases and a structural study suggested that XopQ can hydrolyze a molecule with a ribosyl group (Yu et al., 2014), as demonstrate by in vitro hydrolase activity on the substrate 4-nitrophyenyl β-D-ribofuranoside (Gupta et al., 2015). A recent study demonstrated that HopQ1 can hydrolyze the cytokinin precursor iP-riboside 5'-monophosphate (iPRMP) in vitro and activate cytokinin signaling in vivo, suggesting this as the mechanism for immune suppression (Hann et al., 2014). An alternative hypothesis is that XopQ/HopQ1 virulence function occurs through direct targeting of 14-3-3 proteins. Both HopQ1 and XopQ have been shown to interact with 14-3-3 proteins in vivo following phosphorylation of a 14-3-3 binding site and that this interaction is important for the virulence function (Li et al., 2013a; Teper et al., 2014). As 14-3-3 proteins have a role in the plant immune system (Oh et al., 2010), it has been proposed that one or more of the 14-3-3's are targets of XopQ/HopQ1 and that the virulence function is achieved through modification, degradation or sequestration of these proteins (Teper et al., 2014).

Both XopQ and HopQ1 are recognized in the plants *N. benthamiana* and *N. tabacum* and trigger an avirulence response (Wei et al., 2007; Schwartz et al., 2015). The recognition of XopQ/HopQ1 in *Nicotiana* species is not dependent on interaction with host 14-3-3 proteins, suggesting that 14-3-3 proteins are not involved in the recognition pathway (Li et al., 2013a). Perception of XopQ/HopQ1 in *N. tabacum* is independent of the putative active site of the protein (Li et al., 2013b; Adlung and Bonas, 2017).

SUMMARY

The gene Roq1 from *Nicotiana benthamiana* has been unexpectedly found to mediate the perception of the plant pathogen effector XopQ/HopQ1 and thereby enhance resistance to pathogens containing this or a similar gene, including species of *Xanthomonas, Pseudomonas* and *Ralstonia*, in other plant species. Based on this discovery, a non-*Nicotiana* transgenic plant comprising an exogenous polynucleotide encoding *Nicotiana benthamiana* Roq1 or a variant thereof is provided, as well as seeds from the same.

Also provided is method for enhancing the resistance of a non-*Nicotiana* plant to a plant pathogen strain, species or pathovar containing an effector recognized by Roq1. This method may comprise: (a) introducing an exogenous polynucleotide encoding *Nicotiana benthamiana* Roq1 or variant thereof into the plant cell; and (b) regenerating a transgenic plant from the plant cell.

These and other inventions are described in greater detail below.

BRIEF DESCRIPTION OF THE DRAWINGS

The skilled artisan will understand that the drawings, described below, are for illustration purposes only. The drawings are not intended to limit the scope of the present teachings in any way.

DEFINITIONS

Figure 1:
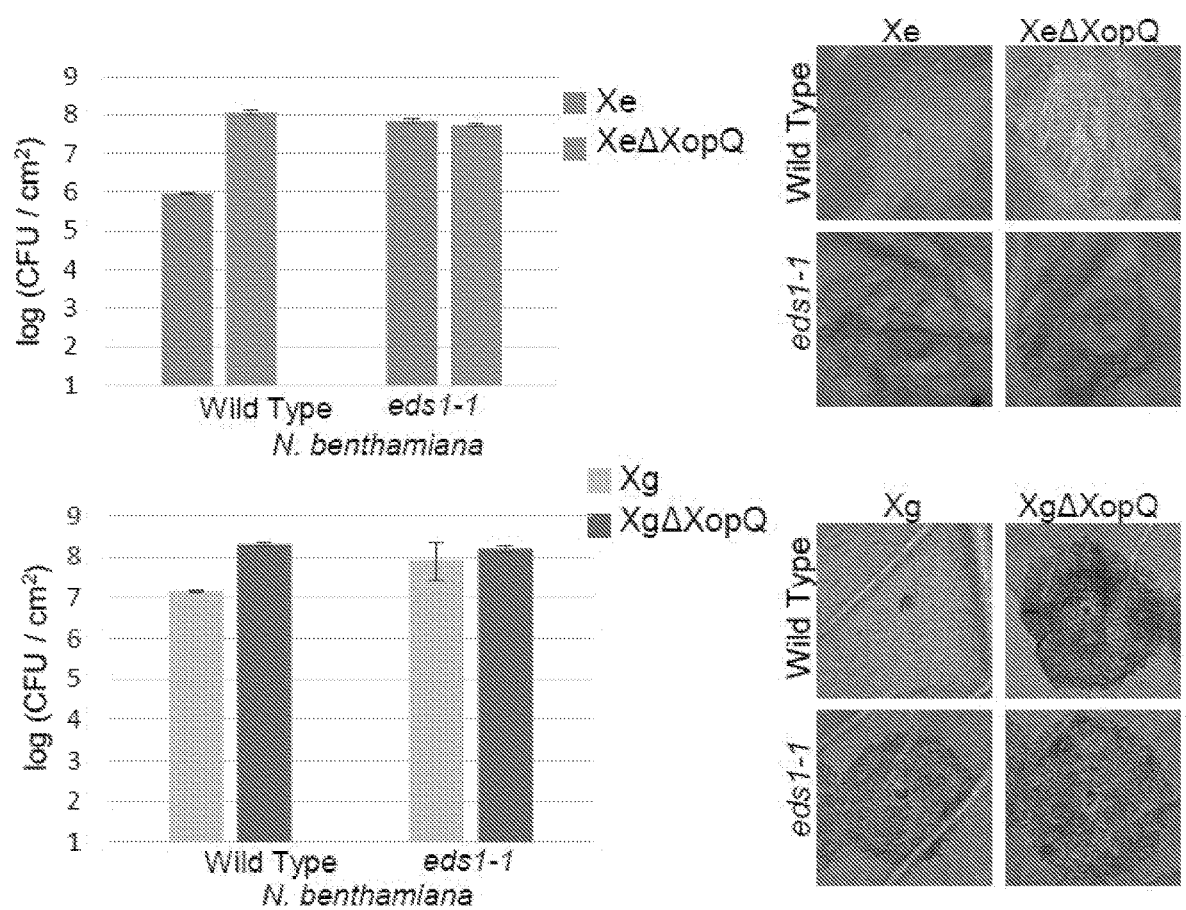
FIG. 1. Effect of XopQ perception on bacterial growth and disease symptoms. *X. euvesicatoria* and *X. gardneri* wild type and XopQ knockout strains were infiltrated into *N. benthamiana* leaves at low inoculum ($OD_{600}$=0.0001). Bacterial growth was assayed at six days post infiltration and disease symptoms were imaged at thirteen and nine days post infiltration for Xe and Xg respectively. Error bars indicate standard deviation from three replicates. CFU—colony forming units.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

As used herein, "resistance" is a relative term in that the presence of a polypeptide of the invention (i) reduces the disease symptoms of a plant comprising the gene (R (resistance) gene) that confers resistance, relative to a plant lacking the R gene, and/or (ii) reduces pathogen reproduction or spread on a plant or within a population of plants comprising the R gene and/or (iii) would act to confer resistance to a particular pathogen in the absence of other resistance mechanism(s). Resistance as used herein is relative to the "susceptible" response of a plant to the same pathogen. Typically, the presence of the R gene improves at least one production trait of a plant comprising the R gene when infected with the pathogen, such as grain yield, when compared to an isogenic plant infected with the pathogen but lacking the R gene. The isogenic plant may have some level of resistance to the pathogen, or may be classified as susceptible. Thus, the terms "resistance" and "enhanced resistance" are generally used herein interchangeably. Furthermore, a polypeptide of the invention does not necessarily confer complete pathogen resistance, for example when some symptoms still occur or there is some pathogen reproduction on infection but at a reduced amount within a plant or a population of plants. Resistance may occur at only some stages of growth of the plant, for example in adult plants (fully grown in size) and less so, or not at all, in seedlings, or at all stages of plant growth. By using a transgenic strategy to express an polypeptide in a plant, the plant of the invention can be provided with resistance throughout its growth and development Enhanced resistance can be determined by a number of methods known in the art such as analysing the plants for the amount of pathogen and/or analysing plant growth or the amount of damage or disease symptoms to a plant in the presence of the pathogen, and comparing one or more of these parameters to an isogenic plant lacking an exogenous gene encoding a polypeptide of the invention.

The terms "non-*Nicotiana* plant" and "not a *Nicotiana* plant" refer to a plant that is not a member of the *Nicotiana* genus of herbaceous plants and shrubs also referred to as "tobacco" plants.

Other definitions of terms may appear throughout the specification.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series*

(Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* 3$^{rd}$ Ed., W. H. Freeman Pub., New York, N.Y. and Berg et al. (2002) *Biochemistry*, 5$^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Provided herein is a transgenic plant comprising an exogenous polynucleotide encoding a polypeptide that is at least 80% identical to (e.g., at least 90% identical to, at least 94% identical to, at least 95% identical to, at least 98% identical to or the same as) the *Nicotiana benthamiana* Roq1 sequence of SEQ ID NO: 1, wherein the plant is not a *Nicotiana* plant.

SEQ ID NO:1 provides the amino acid sequence of the Roq1 protein from *Nicotiana benthamiana* and is shown below. Roq1 orthologs may be found in other species and utilized herein.

```
MLTSSSHHGRSYDVFLSFRGEDTRKTFVGHLFNALIEKGIHTFMDDKELK
RGKSISSELMKAIGESRFAVVVFSKNYASSTWCLEELVKILEIHEKFELI
VVPVFYDVDPSTVRKQNGEYAVCFTKFEANLVDDRDKVLRWREALTKVAN
ISGHDLRNTYNGDESKCIQQILKDIFDKFCFSISITNRDLVGIESQIKKL
SSLLRMDLKGVRLVGIWGMGGVGKTTAARALFNRYYQNFESACFLEDVKE
YLQHHTLLYLQKTLLSKLLKVEFVDCTDTEEMCVILKRRLCSKKVLVVLD
DVNHNDQLDKLVGAEDWFGSGSRIVITTRDMKLLKNHDVHETYEIKVLEK
DEAIELFNLHAFKRSSPEKEFKELLNLVVDYTGGLPLALKVLGSLLYKED
LDVWISTIDRLKDNPEGEIMATLKISFDGLRDYEKSIFLDIACFFRGYNQ
RDMTALFHASGFHPVLGVKTLVEKSLIFILEDKIQMHDLMQEMGRQIAVQ
ESPMRRIYRPEDVKDACIGDMRKEAIEGLLLTEPEQFEEGELEYMYSAEA
LKKTRRLRILVKEYYNRGFDEPVAYLPNSLLWLEWRNYSSNSFPSNFEPS
KLVYLTMKGSSIIELWNGAKRLAFLTTLDLSYCHKLIQTPDFRMITNLER
LILSSCDALVEVHPSVGFLKNLILLNMDHCISLERLPAIIQSECLEVLDL
NYCFNLKMFPEVERNMTHLKKLDLTSTGIRELPASIEHLSSLENLQMHSC
NQLVSLPSSIWRFRNLKISECEKLGSLPEIHGNSNCTRELILKLVSIKEL
PTSIGNLTSLNFLEICNCKTISSLSSSIWGLTSLTTLKLLDCRKLKNLPG
IPNAINHLSGHGLQLLLTLEQPTIYERLDLLRIIDMSWCSCISSLPHNIW
MLKFLRILCISYCSRLEYLPENLGHLEHLEELLADGTGILRLPSSVARLN
KLEVLSERKKFAIGPKVQYSSSMLNLPDDVEGSLGSLGSVVKLNLSGNGF
CNLPETMNQLFCLEYLDITFCQRLEALPELPPSIKELYVDEHLALRIMED
LVIKCKELNLIAVTKIEYQNFYRWLDSIWSDVSELLENSQKQQLDDMLQL
IPFSYLSTAKREEVLKIVIHGTRIPEWFRWQDRSATTMSVNLPEYWYTEN
FLGFAICCSCCFYHSARSYDVEFEGSMHHYNYDSSYWKEYEEPSYDFYER
DSIFITAKLTPRHKGMRTEELKKVCSFSMNVLRRATAVPNMCFAFFPFNS
LCHISNLQANNPNDYGIFETCLSPGDIRHRGKQWGFNLVYKDETGGSVTH
EMLINR*
```

The transgenic plant may be monocotyledonous or dicotyledonous. Target plants include, but are not limited to, the following: cereals (for example, wheat, barley, rye, oats, rice, maize, sorghum and related crops); grapes; beet (sugar beet and fodder beet); pomes, stone fruit and soft fruit (mango, kiwi, apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, peppers, potatoes, paprika); lauraceae (avocados, cinnamon, camphor); or plants such as maize, cassava, nuts (walnut), coffee, sugar cane, tea, vines, hops, turf, bananas and natural rubber plants, as well as ornamentals (flowers, shrubs, broad-leaved trees and evergreens, such as conifers). In many embodiments, the plant may be susceptible to infection by one or more species of *Xanthomonas, Pseudomonas, Ralstonia*, or another pathogen containing an effector with homology to XopQ recognized by Roq1 (e.g., one or more species of *Xanthomonas* and one or more species of *Pseudomonas*) without the exogenous polynucleotide. In some cases the plant may be a hybrid.

As would be apparent, the transgenic plant has enhanced resistance to at least one species of *Xanthomonas, Pseudomonas, Ralstonia*, or another pathogen containing an effector with homology to XopQ which is recognized by Roq1 (e.g., one or more species of *Xanthomonas* and one or more species of *Pseudomonas*), relative to a control plant that is otherwise identical to the transgenic plant but does not contain the exogenous polynucleotide. *Xanthomonas/Pseudomonas* species to which the Roq1 provide resistance to include those that encode a XopQ/HopQ1 polypeptide. These polypeptides appear to be present in many pathogenic strains of *Xanthomonas/Pseudomonas* and, as such, Roq1 is believed to provide resistance to one or more of the bacteria listed in FIG. 6, including, but not limited to, *Xanthomonas gardneri, Xanthomonas perforans, Xanthomonas euvesicatoria, Xanthomonas oryzae* pv *oryzae, Xanthomonas oryzae* pv. *oryzicola, Xanthomonas hortorum, Xanthomonas campestris, Xanthomonas axonopodis, Xanthomonas citri, Xanthomonas arboricola, Xanthomonas asicola, Xanthomonas fragariae, Xanthomonas sacchari* and *Pseudomonas syringae*, as well as *Acidovorax citrulli, Xanthomonas translucens* and *Ralstonia solanacearum*. A list of *Xanthomonas* and *Pseudomonas* to which the plants should have enhanced resistance is set forth in Bull et al. J. Plant Pathology (2010 92: 551-591, which is incorporated by reference for that list.

In some embodiments, the amino acid sequence of the polypeptide may be at least 80% identical to (e.g., 90% identical to, 94% identical to, at least 95% identical to, at least 96% identical to, at least 97% identical to, at least 98% identical to, at least 99% identical to, or 100% identical to)

the amino acid sequence of a wild type Roq1 polypeptide from tobacco, e.g., a Roq1 polypeptide from *N. benthamiana, N. tabacum, N. attenuata,* or *N. tomentosiformis* (the sequences for which are available in Genbank as accession numbers ATD14363.1, XP_019226668.1, XP_009615050.1, and XP_016467297.1).

Methods for making transgenic plants are very well known in the art, as are the choices for promoters and other regulatory regions (see, e.g., US20160076050, US20170218386 and US20160208279). As such, the present plants may be readily implemented by adapting any suitable method. In some embodiments, the exogenous polynucleotide is operably linked to a promoter. The promoter can be exogenous to the plant or endogenous to the plant. In some embodiments, the plant may be made by replacing a coding sequence in the genome of the plant with the exogenous polynucleotide.

Also provided is a seed of a transgenic plant described above. These seeds may be made by selfing the plant or crossing the plant with another plant of the same species to produce, e.g., hybrid seed.

Also provided is a population of at least 100 of the transgenic plants, e.g., at least 1,000, or at least 10,000 of the transgenic plants, growing in a field.

Also provided is a method for enhancing the resistance of a non-*Nicotiana* plant to at least one species of *Xanthomonas* or *Pseudomonas* (e.g., one or more species of *Xanthomonas* and one or more species of *Pseudomonas*). In some embodiments, this method may comprise: (a) introducing an exogenous polynucleotide encoding a polypeptide that is at least 90% identical (e.g., at least 95%, at least 98%, or 100% identical) to the Roq1 sequence of SEQ ID NO: 1 into a plant cell that is from a plant that is susceptible to infection by *Xanthomonas* and/or *Pseudomonas*; and (b) regenerating a transgenic plant from the plant cell.

In some embodiments, the amino acid sequence of the polypeptide may be at least 80% identical to (e.g., at least 90% identical to, at least 95% identical to, at least 95% identical to, at least 96% identical to, at least 97% identical to, at least 98% identical to, at least 99% identical to, or 100% identical to) the amino acid sequence of a tobacco Roq1 polypeptide, e.g., a Roq1 polypeptide from *N. benthamiana, N. tabacum, N. attenuata,* or *N. tomentosiformis*. (the sequences for which are available in Genbank as accession numbers ATD14363.1, XP_019226668.1, XP_009615050.1, and XP_016467297.1).

Roq1 activity appears to require a functional and compatible NRG1 and/or EDS1 gene. As such, a functional NRG1 and/or EDS1 gene can be added to plants that do not already have a functional NRG1 and/or EDS1 gene or that contain a version of these genes which is not compatible with Roq1, in order for Roq1 to be active in immune activation.

As noted above, methods for making transgenic plants are very well known in the art, as are the choices for promoters and other regulatory regions (see, e.g., US20160076050, US20170218386 and US20160208279). As such, the present plants may be readily implemented by adapting any suitable method.

EMBODIMENTS

A transgenic plant comprising an exogenous polynucleotide encoding a polypeptide that is at least 80% identical to the *Nicotiana benthamiana* Roq1 sequence of SEQ ID NO: 1, wherein the plant is not a *Nicotiana* plant.

The transgenic plant of any prior embodiment, wherein the plant has enhanced resistance to at least one species of *Xanthomonas, Pseudomonas, Ralstonia,* or another pathogen containing an effector with homology to XopQ which is recognized by Roq1 relative to a control plant that is otherwise identical to the transgenic plant but does not contain the exogenous polynucleotide.

The transgenic plant of any prior embodiment, wherein the plant has enhanced resistance to at least one species of *Xanthomonas* and at least one species of *Pseudomonas* relative to a control plant that is otherwise identical to the transgenic plant but does not contain the exogenous polynucleotide.

The transgenic plant of any prior embodiment, wherein the plant is a monocot.

The transgenic plant of any prior embodiment, wherein the plant is a dicot.

The transgenic plant of any prior embodiment, wherein the amino acid sequence of the polypeptide is at least 90% identical to the amino acid sequence of the *Nicotiana benthamiana* Roq1 sequence of SEQ ID NO:1

The transgenic plant of any prior embodiment, wherein the amino acid sequence of the polypeptide is at least 94% identical to the amino acid sequence of the *Nicotiana benthamiana* Roq1 sequence of SEQ ID NO:1

The transgenic plant of any prior embodiment, wherein the amino acid sequence of the polypeptide is at least 95% identical to the amino acid sequence of the *Nicotiana benthamiana* Roq1 sequence of SEQ ID NO:1

The transgenic plant of any prior embodiment, wherein the amino acid sequence of the polypeptide is identical to the amino acid sequence of the *Nicotiana benthamiana* Roq1 sequence of SEQ ID NO:1.

The transgenic plant of any prior embodiment, wherein the exogenous polynucleotide is operably linked to a promoter.

The transgenic plant of any prior embodiment, wherein the promoter is exogenous to the plant or wherein the promoter is endogenous to the plant.

A seed of a transgenic plant of any prior embodiment.

A population of at least 100 plants of any prior embodiment, growing in a field.

A method for enhancing the resistance of a non-*Nicotiana* tobacco plant to at least one species of *Xanthomonas, Pseudomonas, Ralstonia,* or another pathogen containing an effector with homology to XopQ which is recognized by Roq1 (e.g., enhancing the resistance to at least one species of *Xanthomonas* and at least one species of *Pseudomonas*), comprising: (a) introducing an exogenous polynucleotide encoding a polypeptide that is at least 80% identical to the *Nicotiana benthamiana* Roq1 sequence of SEQ ID NO: 1 into the plant cell, wherein the plant cell is from a plant that is susceptible to infection by *Xanthomonas, Pseudomonas, Ralstonia,* or another pathogen containing an effector with homology to XopQ which is recognized by Roq1; and (b) regenerating a transgenic plant from the plant cell.

The method of any prior method embodiment, wherein the plant has enhanced resistance to at least one species of *Xanthomonas* or *Pseudomonas* relative to a control plant that is otherwise identical to the transgenic plant but does not contain the exogenous polynucleotide.

The method of any prior method embodiment, wherein the plant has enhanced resistance to at least one species of *Xanthomonas* and at least one species of *Pseudomonas*) relative to a control plant that is otherwise identical to the transgenic plant but does not contain the exogenous polynucleotide.

The method of any prior method embodiment, wherein the plant is a monocot.

The method of any prior method embodiment, wherein the plant is a dicot.

The method of any prior method embodiment, wherein the amino acid sequence of the polypeptide is at least 90% identical to the amino acid sequence of the *Nicotiana benthamiana* Roq1 sequence of SEQ ID NO:1.

The method of any prior method embodiment, wherein the amino acid sequence of the polypeptide is at least 94% identical to the amino acid sequence of the *Nicotiana benthamiana* Roq1 sequence of SEQ ID NO:1.

The method of any prior method embodiment, wherein the amino acid sequence of the polypeptide is at least 95% identical to the amino acid sequence of the *Nicotiana benthamiana* Roq1 sequence of SEQ ID NO:1

The method of any prior method embodiment, wherein the amino acid sequence of the polypeptide is identical to the amino acid sequence of the *Nicotiana benthamiana* Roq1 sequence of SEQ ID NO:1.

The method of any prior method embodiment, wherein the exogenous polynucleotide is operably linked to a promoter.

The method of any prior method embodiment, wherein the promoter is exogenous to the plant or wherein the promoter is endogenous to the plant.

The transgenic plant, seed, or method of any prior embodiment, wherein the plant is a cereal (for example, wheat, barley, rye, oats, rice, maize, sorghum and related crops); a grape; a beet (sugar beet and fodder beet); a pome, a stone fruit and a soft fruit (mango, kiwi, apple, pear, plum, peach, almond, cherry, strawberry, raspberry and blackberry); leguminous plant (bean, lentil, pea, soybean); oil plant (rape or other Brassicas, mustard, poppy, olive, sunflower, safflower, flax, coconut, castor oil plant, cocoa bean, groundnut); cucumber plant (marrow, cucumber, melon); fibre plant (cotton, flax, hemp, jute); citrus fruit (orange, lemon, grapefruit, mandarin); a vegetable (spinach, lettuce, asparagus, cabbage, carrot, onion, tomato, pepper, potato, paprika); a lauraceae (avocado, cinnamon, camphor); or a plant such as maize, cassava, nuts (walnut), coffee, sugar cane, tea, vines, hops, turf, banana or a natural rubber plant, or an ornamental (flower, shrub, broad-leaved tree or evergreen).

In any embodiment, the exogenous polynucleotide may additionally provide resistance to other pathogen species containing an effector with homology to XopQ which is recognized by Roq1, such as species of the genus *Ralstonia*, e.g, *Ralstonia solanacearum*. As such, in transgenic plant embodiments, the plant may have enhanced resistance to at least one species of *Xanthomonas*, at least one species of *Pseudomonas* and at least one species of *Ralstonia*, relative to a control plant that is otherwise identical to the transgenic plant but does not contain the exogenous polynucleotide

EXAMPLES

Aspects of the present teachings can be further understood in light of the following examples, which should not be construed as limiting the scope of the present teachings in any way.

In this study the perception pathway of XopQ in *N. benthamiana* was investigated. Using the CRISPR/CAS9 system (Jinek et al., 2012), a stable eds1 mutants of *N. benthamiana* was created which were unable to perceive XopQ/HopQ1, thereby implicating a TLR in the perception of these effectors as was recently reported (Adlung and Bonas, 2016). A reverse genetic screen was conducted using Viral Induced Gene Silencing (VIGS) of the TLRs in *N. benthamiana*. A single TLR was identified which is required for the perception of XopQ. Biochemical experiments suggest that this protein, named Recognition of XopQ (Roq1), directly interacts with XopQ and HopQ1. Expression of Roq1 in other plant species is sufficient to enable the perception of diverse XopQ/HopQ1/RipB alleles, suggesting this gene may be useful for engineering resistance against *Xanthomonas, Pseudomonas, Ralstonia* and other pathogens containing a Roq1-recognized homolog of XopQ in many different crop species.

Results

Perception of XopQ depends on EDS1. The *Xanthomonas* effector protein XopQ and the close homolog HopQ1 from *Pseudomonas* have previously been shown to trigger an avirulence response in *N. benthamiana*, indicating the presence of an immune perception pathway capable of detecting XopQ. To test if this pathway is dependent on eds1, a growth assay using wild type *Xanthomonas euvesicatoria* and the XopQ knockout was performed on both *N. benthamiana* wild type and eds1 mutant plants. Wild type *X. euvesicatoria* grew approximately 100-fold more on the eds1 mutant than the wild type plants, whereas the XopQ knockout grew to similarly high levels on both the wild type and eds1 plant (FIG. 1). Similar but less pronounced results were observed for *X. gardneri*, which grew 10-fold more in the absence of either EDS1 or XopQ (FIG. 1).

Figure 2:
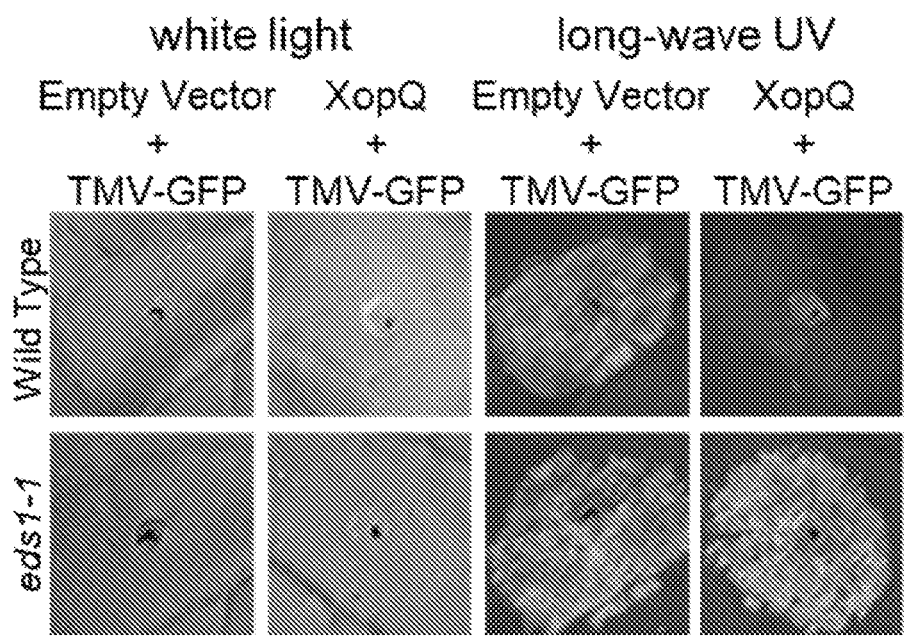
FIG. 2. GFP-based reporter for immune activation. GFP-TMV was co-expressed with an empty vector or XopQ transiently using *Agrobacterium* in wild type and eds1-1 mutant *N. benthamiana* leaves. The leaves were imaged three days post infiltration under white light (left) or long-wave UV (right) using a handheld digital camera.

Development of a fluorescence-based assay for XopQ perception. Unlike some recognized effector proteins that give a strong visible cell death response when transiently expressed, expression of XopQ in wild type *N. benthamiana* typically gives a mild chlorotic phenotype not well suited for a screen (FIG. 2). The disease symptoms observed to be associated with a loss of XopQ recognition do give a strong visible response (FIG. 1), but this assay was found to be inconsistent on Viral-Induced Gene Silencing (VIGS) plants, possibly due to only a partial knockdown of the target gene. An alternative assay was designed in which the XopQ protein was transiently expressed along with a Tobacco Mosaic Virus replicon containing a GFP gene (Marillonnet et al., 2005). In wild type plants XopQ perception resulted in immune activation and a lack of visible GFP from the viral replicon (FIG. 2). Lack of XopQ perception in the eds1 mutant allowed for strong GFP fluorescence to be observed using a handheld long-wave UV light. This phenotype was very robust in the eds1 mutants and consistent, though weaker, in EDS1 VIGS plants. This assay was employed to a reverse genetic screen of the TLR genes in *N. benthamiana* to identify the immune recognition receptor for XopQ.

Figure 3:
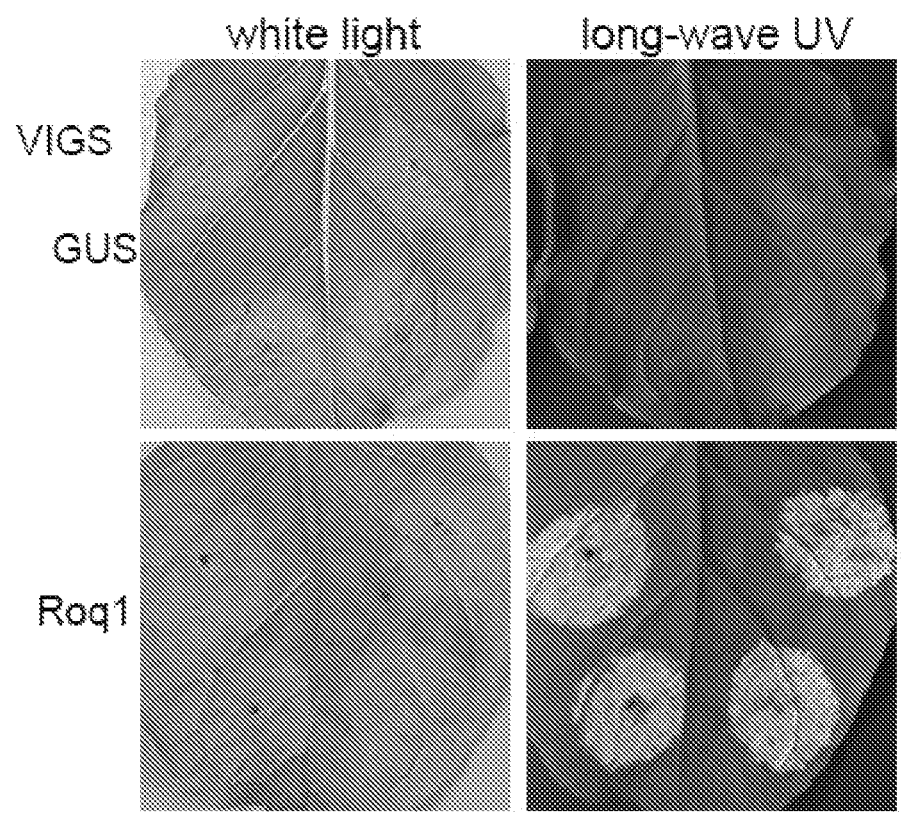
FIG. 3. GFP-TMV reporter in VIGS leaves of *N. benthamiana*. Viral-Induced Gene Silencing was used to down-regulate either the GUS gene (as a negative control, top) or Roq1 (bottom). XopQ was transiently expressed along with the TMV-GFP reporter using *Agrobacterium* and the plants were imaged at four days post infiltration under white light (left) or long-wave UV (right).

Identification of a TLR required for XopQ perception. VIGS constructs were designed to target all TLR genes in *N. benthamiana*. Nine VIGS constructs were cloned with fragments of up to four TLRs each. In this initial screen one of the nine constructs, targeting three distinct TLRs, was found to consistently prevent perception of XopQ and allow for expression of the GFP reporter. Individual VIGS constructs were made for these three candidate genes and one was found to prevent XopQ perception (FIG. 3). The gene targeted by this construct was named Recognition of XopQ1 (Roq1). Putative orthologs of Roq1 were identified in several other *Nicotiana* species but were absent in *Solanum lycopersicum, Solanum tuberosum, Capsicum annuum* and all other non-*Nicotiana* species examined.

Figure 4:
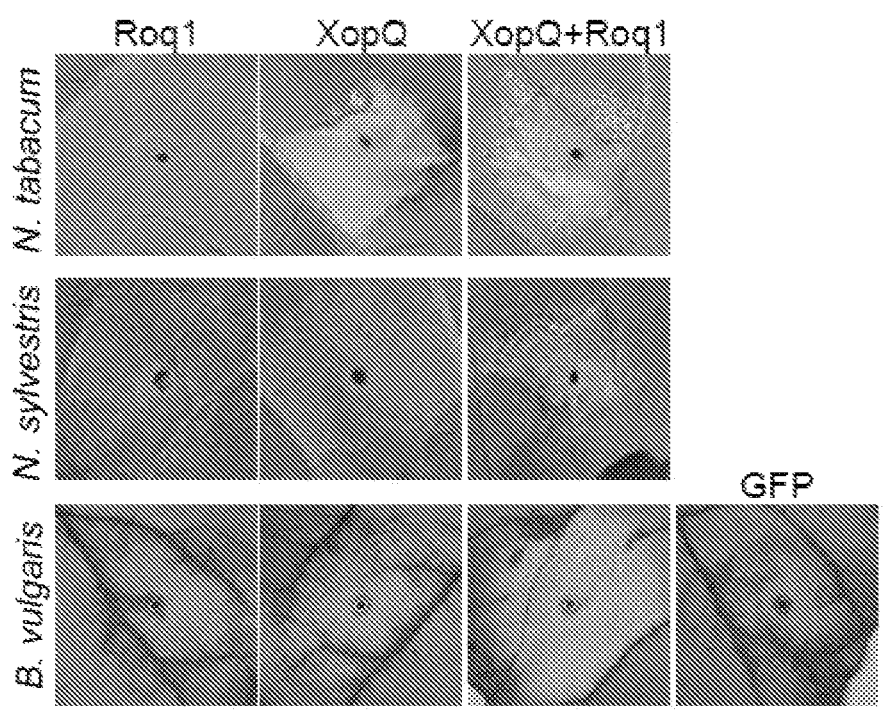
FIG. 4. Transient expression of Roq1 and XopQ. Roq1 and XopQ were transiently expressed using *Agrobacterium* in leaf tissue of *N. tabacum*, *N. sylvestris* and *B. vulgaris*. The *Agrobacterium* was infiltrated at a total $OD_{600}$ of 0.5 and the plants were imaged at six days post infiltration for *N. tabacum* and *N. sylvestris*, and nine days post infiltration for *B. vulgaris*.
Figure 7:
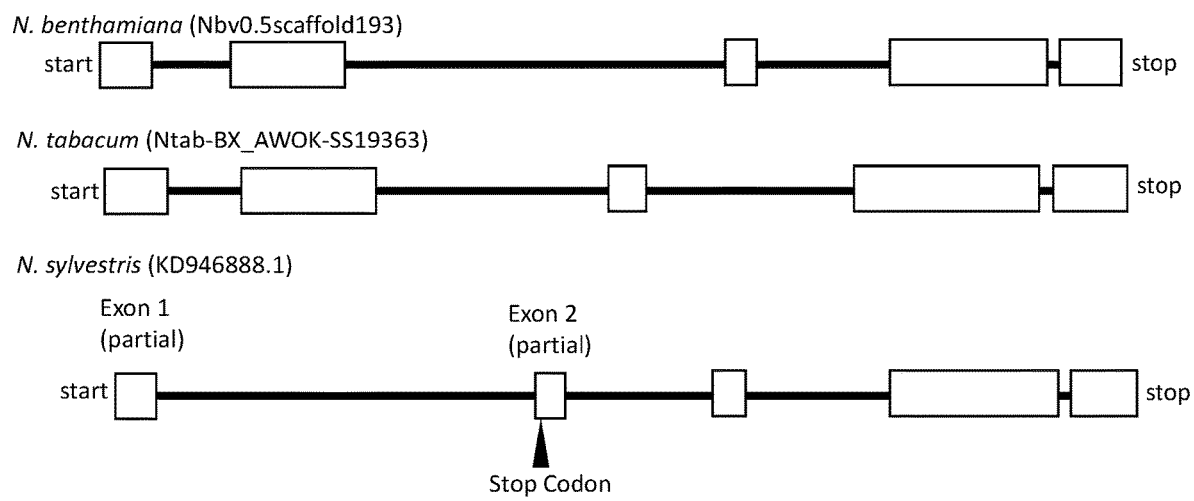
FIG. 7 (A-B): Roq1 gene models. (A) The gene models for Roq1 from *Nicotiana benthamiana*, the highly similar ortholog from *Nicotiana tabacum* and the putative pseudogene from *Nicotiana sylvestris* are shown. The Roq1 gene contains five exons (depicted as white-filled box) and four introns. The predicted CDS for Roq1 is 3921 bp and the gene spans a predicted 9.6 kb from the start codon to the stop codon. The *N. sylvestris* gene contains a predicted stop codon in exon 2 and is missing part of exon 1 and most of exon 2 (B, aberrant sequences boxed). An aberrant, 8.7 kb insert is present between exon1 and exon2 in the *N. sylvestris* gene. The genomic sequence from *N. benthamiana* was obtained from Benth Genome website, the *N. tabacum* sequence from Sol Genomics and the *N. sylvestris* sequence was obtained from NCBI. Accession numbers for the genome scaffolds are shown in parentheses for each. SEQ ID NOS. 2-7.

Roq1 is sufficient to allow perception of XopQ in *Nicotiana sylvestris* and *Beta vulgaris*. While highly conserved orthologs of Roq1 were identified in several other *Nicotiana* species including *N. tabacum, N. attenuata*, and *N. tomentosiformis*, the copy of Roq1 from *N. sylvestris* was found to contain an aberrant sequence disrupting the first and second exons, as well as a stop codon in a conserved part of the second exon (FIG. 7). Disruption of the endogenous Roq1 gene in *N. sylvestris* is consistent with a previous report that this species is unable to perceive XopQ (Adlung and Bonas, 2016). Transient expression of the *N. benthamiana* Roq1 gene along with XopQ in *N. sylvestris* resulted in a visible hypersensitive response that was not present when either Roq1 or XopQ were expressed alone (FIG. 4). To determine if Roq1 can be used to enable perception of XopQ in plants outside of the *Nicotiana* genus, Roq1 was co-expressed with XopQ in *Beta vulgaris*. This resulted in a chlorotic effect similar to that observed when XopQ is expressed in wild type *N. benthamiana* leaves (FIG. 4).

Roq1 co-immunoprecipitates with XopQ. The recognition of HopQ1 in *N. tabacum* has previously been shown to be independent of HopQ1 activity (Li et al., 2013b). It was hypothesized that Roq1 may directly interact with XopQ instead of "Guarding" a protein or molecule that is modified by this effector. To test this, a series of co-immunoprecipitation experiments in eds1-1 *N. benthamiana* were performed. Roq1-6xHA was found to be pulled down by both XopQ-3xFlag and HopQ1-3xFlag, but not by ATR1-3xFlag, an effector known to interact with the TLR RPP1 (FIG. 5) (Krasileva et al., 2010). ATR1-3xFlag was found to be able to pull down RPP1-6xHA, consistent with previous results, but not Roq1-6xHA.

Figure 6:
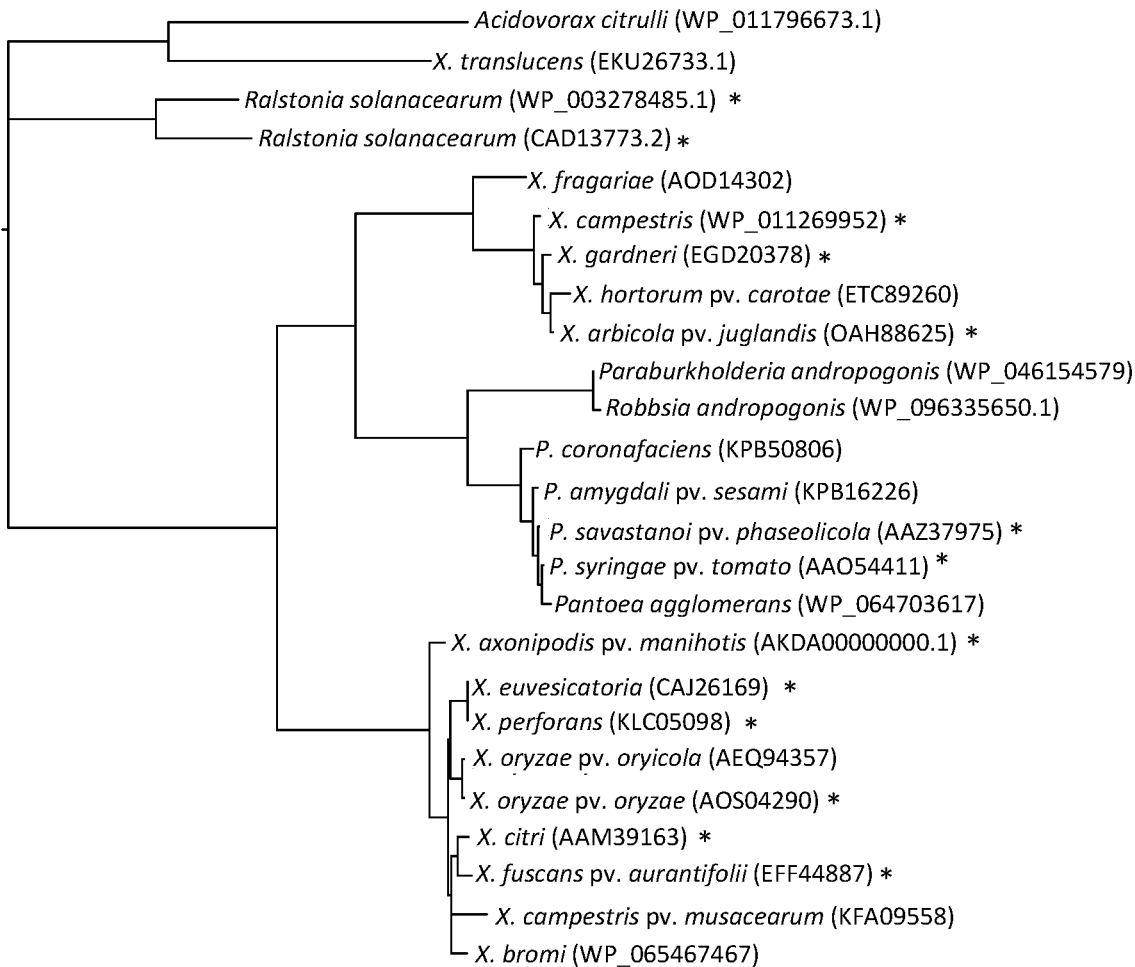
FIG. 6: XopQ phylogenetic tree. XopQ homologs were identified by BLAST search and used to generate a phylogenetic tree. Sequences identified with * were cloned and tested for their ability to be recognized by Roq1. All tested homologs of XopQ elicited a Roq1-dependent immune response. Genbank accession numbers for the various sequences are in brackets next to the species name.
Figure 8:
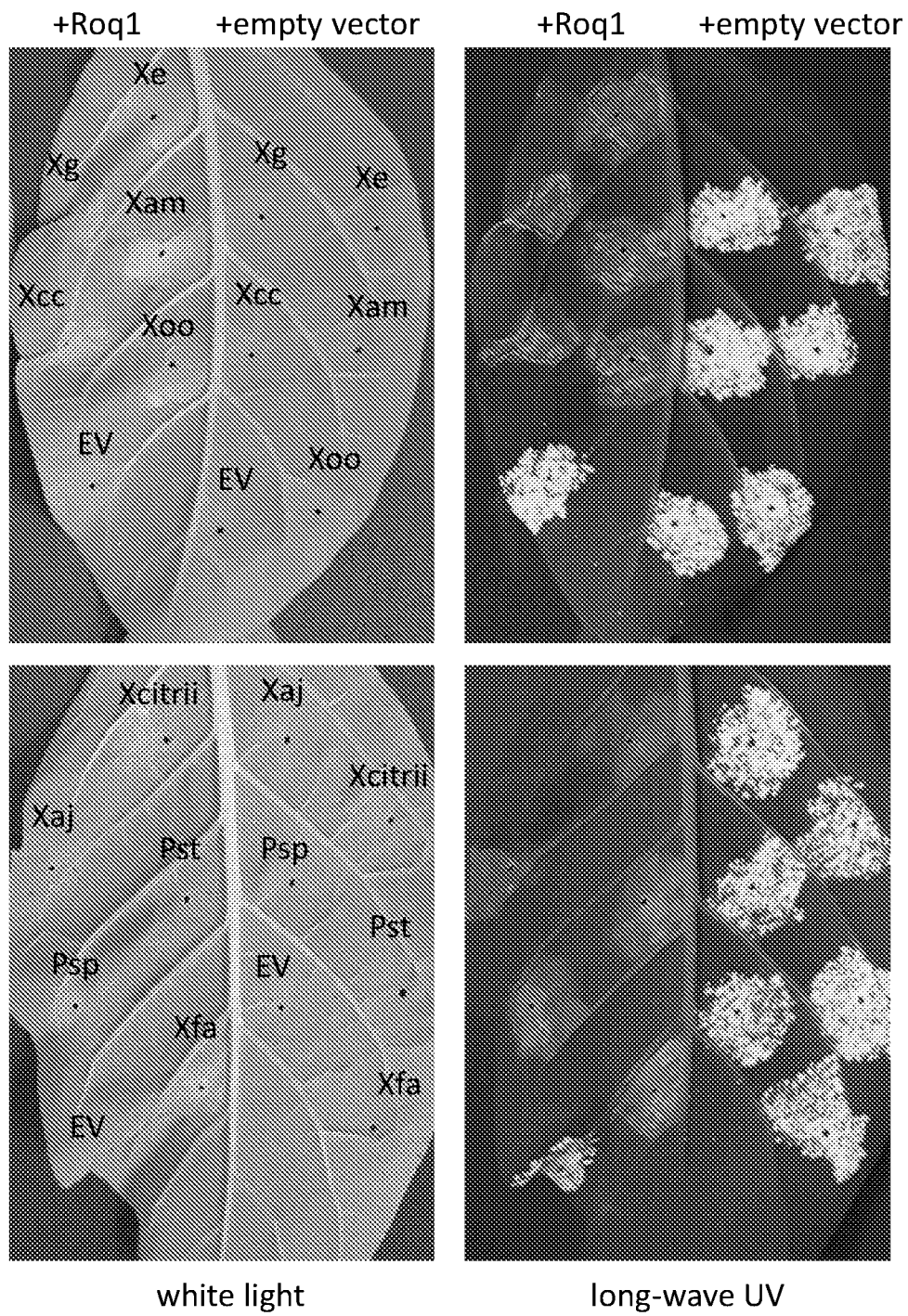
FIG. 8: Roq1 perception of XopQ/HopQ1 alleles. The indicated XopQ/HopQ1 alleles were cloned and transiently expressed along with the GFP-TMV reporter and either Roq1 or an empty vector in *Nicotiana sylvestris*. The leaves were imaged at six days post infiltration under white light and long-wave UV to view the visible HR response and viral GFP expression. *Agrobacterium* harboring the expression constructs was infiltrated at an $OD_{600}$ of 0.05 for each of the three TMV-GFP constructs and 0.3 for the other elicitor/receptor constructs. Xe—*X. euvsicatoria*, Xg—*X. gardneri*, Xam—*X. axonipodis* pv. *manihotis*, Xcc—*X. campestris* pv. *campestris*, Xoo—*X. oryzae* pv. *oryzae*, EV—empty vector, Xaj—*X. axonopodis* pv. *juglandis*, Xcitrii—*X. citrii*, Psp—*P. syringae* pv. *phaseolicola*, Pst—*P. syringae* pv. *tomato*, Xfa—*X. fuscans* subsp. *aurantifolii*.
Figure 9:
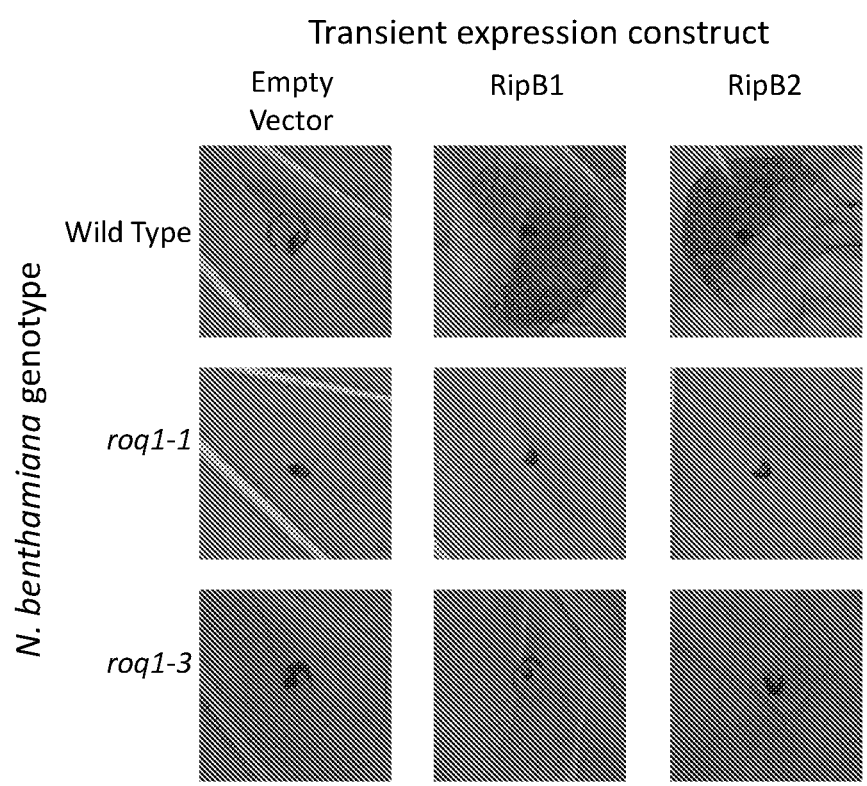
FIG. 9: Roq1 mediates recognition of the *Ralstonia solanacearum* effector RipB. Two alleles of the *Ralstonia solanacearum* effector RipB (WP_003278485.1 and CAD13773.2) we cloned and transiently expressed in *N. benthamiana* using *Agrobacterium*. Expression of both RipB alleles resulted in a visible immune response in wild type plants but was not observed plants homozygous for loss of function mutations in the Roq1 gene. This indicates that Roq1 mediates recognition of the *Ralstonia solanacearum* effector RipB.

Roq1 can mediate the perception of diverse proteins with homology to XopQ. Homologous alleles of XopQ, HopQ1 and RipB are widely distributed among *Xanthomonas, Pseudomonas* and *Ralstonia* species that are pathogenic on various crops. This suggests that Roq1 may be useful to engineer resistance into these crops species, but depends on Roq1 being able to recognize these diverse alleles. To sample the diversity of XopQ proteins a phylogenetic tree was generated and select XopQ and HopQ1 alleles for transient expression. Out of thirteen XopQ/HopQ1 alleles cloned, all elicited a with a Roq1-dependent immune response in *N. benthamiana* or *N. sylvestris* (FIG. 6, FIG. 8).

Figure 11:
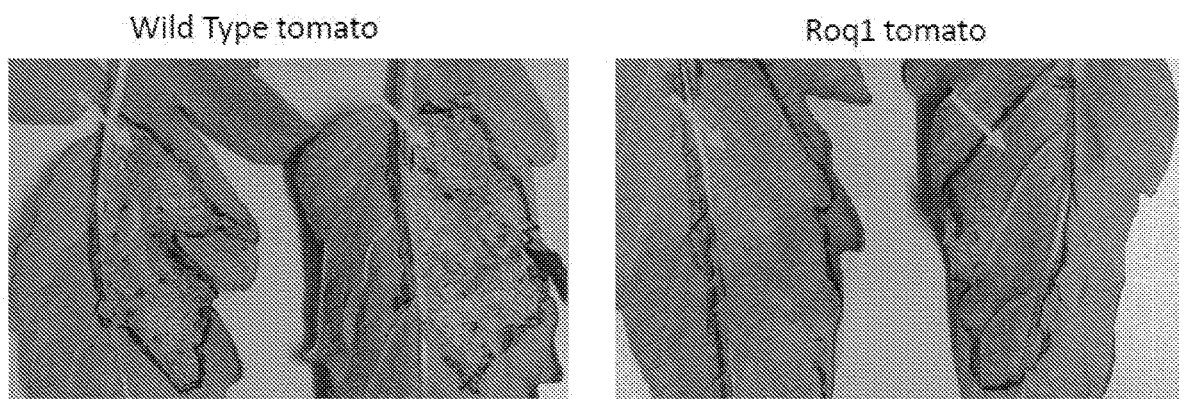
FIG. 11: Visible disease symptoms were imaged at six days post infiltration of *Pseudomonas syringae* pv tomato at an $OD_{600}$ of 0.0001. Wild type tomato leaves (left) have visible necrotic disease lesions in the infiltrated region, marked with an arrow and outline in black marker. The Roq1 tomato plants (right) do not develop disease lesions, indicating that they are resistant to this pathogen.

Expression of Roq1 confers disease resistance against *Pseudomonas syringae*. With reference to FIG. 11, wild type tomato leaves (left) and Roq1-expressing tomato leaves (right) were infiltrated with *Pseudomonas syringae* pv. *tomato*. Six days after inoculation, disease symptoms are clearly visible in the infiltrated area in the wild type leaves (left), whereas no symptoms are visible on the Roq1-transgenic plants (right). The infiltrated parts of the leaves were delimited with black marker and marked with an arrow. Circular wounds visible in the leaves are from the inoculation procedure and not a result of disease symptoms.

Figure 10:
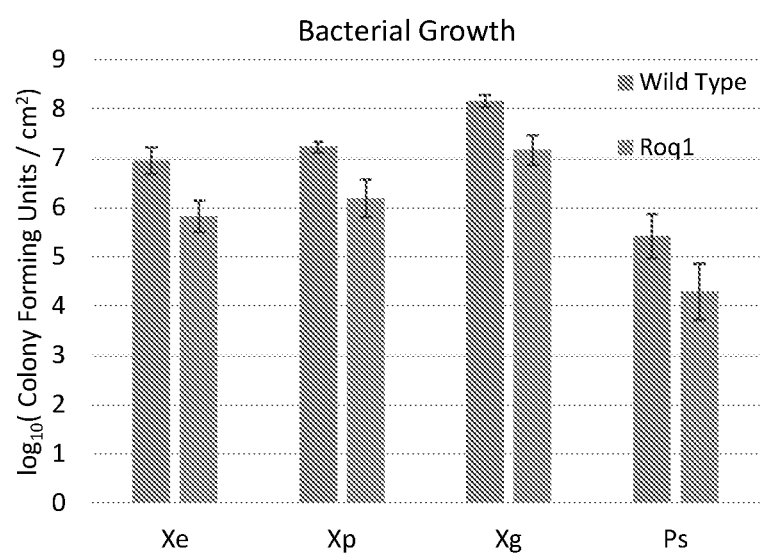
FIG. 10: Roq1 confers resistance to several bacterial pathogens in tomato. *Xanthomonas euvesiactoria* (Xe), *Xanthomonas perforans* (Xp), *Xanthomonas gardneri* (Xg) and *Pseudomonas syringae* pv tomato (Ps) were infiltrated into leaf tissue of wild type and Roq1 tomato plants. Bacterial growth was quantified after four days (Ps) or six days (Xe, Xp, Xg). The tomato plants expressing Roq1 were found to have approximately ten-fold fewer bacteria, indicating that Roq1 confers resistance to these bacteria.

Roq1 confers resistance to pathogens containing a recognized homolog of XopQ. With reference to FIG. 10, bacterial pathogens *Xanthomonas euvesicatoria* (Xe), *Xanthomonas perforans* (Xp), *Xanthomonas gardneri* (Xg) and *Pseudomonas syringae* pv. *tomato* (Ps) were infiltrated into the leaves of wild type tomato plants and tomato plants expressing Roq1. After six days, the leaf tissue was homogenized in buffer and plated to determine bacterial abundance. Approximately ten-fold fewer bacteria were detected in the Roq1 tomato leaves compared to the wild type, indicating that Roq1 confers disease resistance to these pathogens. All of these bacterial have a homolog of XopQ that is recognized by Roq1. Error bars indicated standard deviation.

Roq1 activity depends on EDS1 and NRG1. With reference to FIG. 11, XopQ was transiently expressed in *N. benthamiana* leaf tissue using *Agrobacterium*. Following infiltration, leaves were covered in foil for three days before imaging. Activation of Roq1 leads to a strong immune activation, visible as a cell death response (top) in VIGS negative control plants. Silencing either EDS1 or NRG1 blocks Roq1 activation, indicating that both may be required Roq1 activity and that functional and compatible versions of these genes may need to be added along with Roq1 into a plant species to enable Roq1 function.

Methods

CAS9 mediated knockout of EDS1 and Roq1. Guides to target the *N. benthamiana* EDS1 and Roq1 genes were designed and cloned into entry plasmids containing the CAS9 gene and the *Arabidopsis thaliana* U6-26 promoter to drive guide expression. LR reactions were performed to move the guide and CAS9 cassette into a binary vector which was used for stable transformation into *N. benthamiana* by *Agrobacterium* co-cultivation. Transformed plants were genotyped by PCR and Sanger sequencing, and homozygous knockout lines were obtained from the T1 generation Viral Induced Gene Silencing. Target TLR genes from *N. benthamaiana* were identified using a BLAST search of a transcript database (Nakasugi et al., 2013). The predicted protein sequences of identified genes were aligned and manually curated to remove gene fragments and pseudogenes. Candidate TLRs were targeted for silencing by cloning approximately 300 bp into the TRV2 VIGS vector (Liu et al., 2002) using restriction ligation cloning with the enzyme BsaI. The plasmids were transformed into *Agrobacterium tumefaciens* strain GV3101 and infiltrated into *N. benthamiana* plants along with TRV1 at an $OD_{600}$ of 0.2 each. The plants were infiltrated at 4-6 weeks of age and phenotyped 2-4 weeks after infiltration.

GFP-reporter assay for XopQ perception. *Agrobacterium* harboring the vectors pICH2011, pICH14011, and pICH7410 (Marillonnet et al., 2005) was mixed to a final $OD_{600}$ of 0.05 each along with an *Agrobacterium* strain for transient expression of XopQ at an $OD_{600}$ of 0.3. The mixture was infiltrated into leaf tissue and imaged under long-wave UV light to visualize GFP expression.

Growth assay. To assay bacterial growth, *Xanthomonas* was grown overnight in NYG (0.5% peptone, 0.3% yeast extract, 2% glycerol) with 100 μg/mL rifampcin on a shaker at 30° C. The cultures were spun down at 10,000 g, washed once with 10 mM $MgCl_2$, and infiltrated into leaf tissue at $OD_{600}$=0.0001. Leaf punches were collected at 6 days post infiltration, homogenized, and serially diluted before plating on NYG agar plates with 100 μg/mL rifampcin and 50 μg/mL cycloheximide Colonies were counted 3-4 days after plating.

Transient expression using *Agrobacterium*. *Agrobacterium* cultures were grown overnight in LB with selection at 30° C. on a shaker. Cells were pelleted by centrifugation at 10,000 g and resuspended in infiltration buffer (10 mM $MgCl_2$, 10 mM MES pH 5.6). The cells were diluted to the appropriate $OD_{600}$ and infiltrated into leaf tissue using a needleless syringe.

Plant material and bacteria strains. *Nicotiana sylvestris* was obtained from Select Seeds Co. in Union, Conn. USA ("Woodland Tobacco 346"). *Nicotiana tabacum* and *Beta* vulgaris "Detroit Dark Red, Morse's Strain" (Plantation Products, Norton Mass., USA) were used for transient expression. *X. euvesicatoria* 85-10 and *X. gardneri* 153 were used for pathogen assays. The *X. euvesicatoria* 85-10 ΔXopQ knockout was constructed previously (Schwartz et al., 2015). *Agrobacterium tumefaciens* strains GV3101 and C58C1 were used for transient expression and VIGS.

XopQ knockout in *X. gardneri*. 1000 bp regions upstream and downstream of the XopQ coding sequence were cloned into the pLVC18 plasmid (Lindgren et al., 1986) containing a SacB counter-selectable marker. This plasmid was conjugated into *X. gardneri* and single crossover events were selected for by tetracycline resistance (10 µg/mL) and PCR. Colonies were plated onto NYG media containing 5% sucrose to select for a second crossover event and screened by PCR to identify XopQ deletion strains.

Co-immunoprecipitation assay. Each tissue sample (0.5 g) was ground with mortar and pestle to a homogeneous powder in liquid nitrogen. The samples were suspended in 1 mL of the protein extraction buffer (50 mM Tris-HCl, pH 7.5, 150 mM NaCl, 0.1% Triton X-100, 0.2% Nonidet P-40, 6 mM β-mercaptoethanol, 1× protease inhibitor cocktail). Samples were centrifuged twice (10 min, 14,000 rpm, 4° C.). The supernatant was then transferred to a new tube with 10 µL Flag beads (A2220, Sigma) and incubated at 4° C. for 3 hours. The samples were centrifuged (1 min, 1,000 g) then washed three times with 1 mL of the protein extraction buffer. The protein was eluted by boiling for 5 min in 50 µl of 3× Laemmli buffer, centrifuged and loaded for Western blot. For the anti-Flag Western, the primary antibody was F7425 (Sigma) and the secondary antibody was A0545 (Sigma).

DISCUSSION

Figure 5:
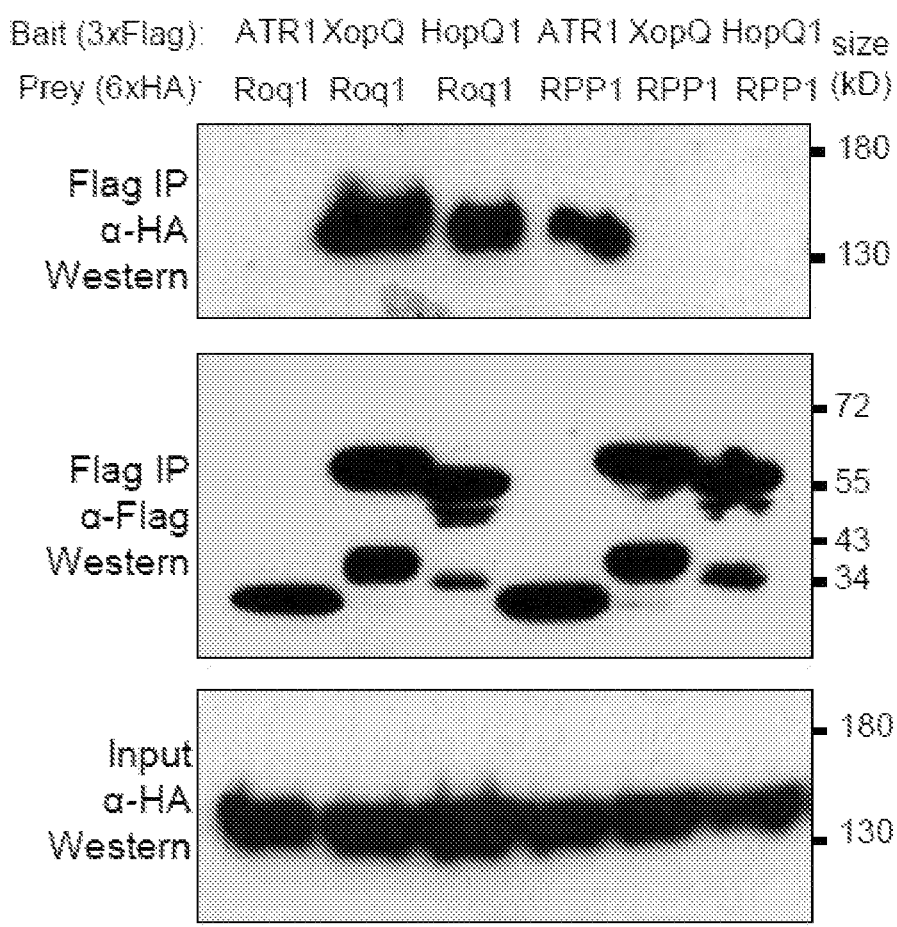
FIG. 5: Co-immunoprecipitation of XopQ and Roq1. XopQ-3×Flag, ATR1-3×Flag and HopQ1-3×Flag were transiently co-expressed with either Rpp1-6×HA or Roq1-6×HA in the *N. benthamiana* eds1 mutant. Western blots with α-HA primary antibody (top) and α-Flag primary antibody (middle) show proteins pulled down with anti-Flag beads for each combination. A Western blot of the input protein extract (prior to precipitation) is shown on the bottom. The *Arabidopsis* NLR protein RPP1 and its cognate effector ATR1 were included as controls. Predicted molecular weights are as follows: XopQ-3×Flag 53 kD, HopQ1-3×Flag 52kD, ATR1-3×Flag 33kD, RPP1-6×HA 145 kD, and Roq1-6×HA 159 kD.

Mechanism of Roq1 recognition of XopQ. Co-immunoprecipitation experiments showed that Roq1 can interact with either XopQ/HopQ1 as determined by immunoprecipitation after transient co-expression in *N. benthamiana* (FIG. 5). Roq1 did not interact with ATR1, indicating that there is specificity and that Roq1 is not interacting with the beads during the procedure. Furthermore, XopQ and HopQ1 did not interact with the TLR protein RPP1, indicating these proteins have some specificity to Roq1 and are not able to pull down all TLR proteins. This data is consistent with the model that Roq1 directly interacts with XopQ during activation. While the various XopQ/HopQ1 alleles have significant amino acid variation, especially at the N terminus, there are highly conserved regions which could mediate Roq1 recognition (data not shown). *X. euvesicatoria* XopQ and *P. syringae* pv. *tomato* HopQ1 share 65% amino acid identity with the variable N terminal region removed. While the EDS1 protein is required for perception of XopQ, it is not required for interaction between Roq1 and XopQ or RPP1 and ATR1. This data supports a model in which EDS1 is involved in the signaling process downstream of the TLR proteins and is not required for expression or proper folding of TLRs. NRG1 has been demonstrated to be required for the function of other TLRs and is believed to be a downstream signaling component (Peart et al., 2005; Qi et al., 2018).

Distribution and specificity of Roq1. The Roq1 gene is highly conserved in several *Nicotiana* species but was not detected in any species outside this genus. This suggests that Roq1 evolved within the *Nicotiana* lineage and is consistent with the previous observation that XopQ failed to elicit an immune response when expressed in non-*Nicotiana* species (Adlung and Bonas, 2016). The wide distribution and high conservation of XopQ homologs in *Xanthomonas*, *Pseudomonas* and other pathogens may be a consequence of the narrow distribution of the Roq1 gene. The observation that co-expression of Roq1 with various XopQ homologs can elicit a Roq1-dependent immune response indicates that Roq1 is able to recognize the different homologs despite the various amino acid differences (FIG. 6, FIG. 8).

Figure 12:
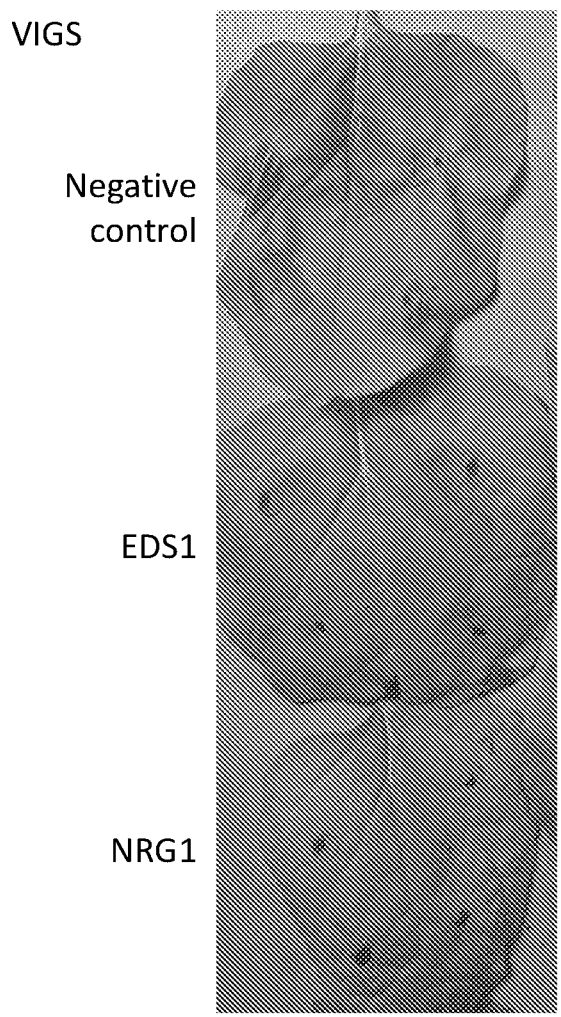
FIG. 12: The Roq1 signaling pathway depends on EDS1 and NRG1. Viral Induced Gene Silencing (VIGS) was used to silence the EDS1 and NRG1 genes in *N. benthamiana*. Relative to the negative control, these plants were unable to perceive transiently expressed XopQ as observed by the lack of a visible immune response. This indicates that both EDS1 and NRG1 are required for Roq1-dependent perception of XopQ.

Use of Roq1 to confer resistance against pathogens with homologs of XopQ. Because Roq1 is able to recognize diverse XopQ homologs (FIG. 6, FIG. 8), this gene likely can be used in many crop species to confer resistance against pathogens containing these or similar effector genes. Because Roq1 likely directly interacts with XopQ, Roq1 may be able to function in a distantly related plant species without the requirement for the transfer of additional signaling components (Wulff et al., 2011). This is supported by the observation that co-expression of Roq1 and XopQ triggers a visible reaction, presumably an immune response, in *Beta vulgaris* (FIG. 6). Roq1 activity does depend on the downstream signaling components such as EDS1 (FIG. 1, FIG. 2, FIG. 12) and SGT1, and NRG1 (FIG. 12). These genes are found in many plant species and therefore in some cases, including tomato, the endogenous EDS1 and NRG1 genes are sufficient for Roq1 function. In other species, particularly in plants more distantly related from the Solanaceous plants, exogenous copies of EDS1 and/or NRG1 may be required to enable Roq1 function.

REFERENCES

Adlung, N., and Bonas, U. (2016). Non-host Resistance Induced by the *Xanthomonas* Effector XopQ Is Widespread within the Genus *Nicotiana* and Functionally Depends on EDS1. *Front. Plant Sci.* 7.

Adlung, N., and Bonas, U. (2017). Dissecting virulence function from recognition—cell death suppression in *Nicotiana benthamiana* by XopQ/HopQ1-family effectors relies on EDS1-dependent immunity. *Plant J.* 38:42-49.

Alfano, J. R., and Collmer, A. (2004). Type III secretion system effector proteins: double agents in bacterial disease and plant defense. *Annu. Rev. Phytopathol.* 42:385-414.

Block, A., Li, G., Fu, Z. Q., and Alfano, J. R. (2008). Phytopathogen type III effector weaponry and their plant targets. *Curr. Opin. Plant Biol.* 11:396-403.

Chisholm, S. T., Coaker, G., Day, B., and Staskawicz, B. J. (2006). Host-microbe interactions: Shaping the evolution of the plant immune response. *Cell* 124:803-814.

Dangl, J. L., Horvath, D. M., and Staskawicz, B. J. (2013). Pivoting the Plant Immune System from Dissection to Deployment 563:7931-7935.

Gupta, M. K., Nathawat, R., Sinha, D., Hague, A. S., Sankaranarayanan, R., and Sonti, R. V (2015). Mutations in the Predicted Active Site of *Xanthomonas oryzae* pv. *oryzae* XopQ Differentially Affect Virulence, Suppression of Host Innate Immunity, and Induction of the HR in a Nonhost Plant. *Mol Plant-Microbe Interact.* 28:195-206.

Gürlebeck, D., Thieme, F., and Bonas, U. (2006). Type III effector proteins from the plant pathogen *Xanthomonas* and their role in the interaction with the host plant. *J. Plant Physiol.* 163:233-55.

Hann, D. R., Dominguez-Ferreras, A., Motyka, V., Dobrev, P. I., Schornack, S., Jehle, A., Felix, G., Chinchilla, D., Rathjen, J. P., and Boller, T. (2014). The *Pseudomonas* type III effector HopQ1 activates cytokinin signaling and interferes with plant innate immunity. *New Phytol.* 201: 585-598.

Jinek, M., Chylinski, K., Fonfara, I., Hauer, M., Doudna, J. A., and Charpentier, E. (2012). A Programmable Dual-RNA—Guided 337:816-822.

Jones, J. D. G., and Dangl, J. L. (2006). The plant immune system. *Nature* 444:323-329.

Jones, J. D. G., Witek, K., Verweij, W., Jupe, F., Cooke, D., Dorling, S., Tomlinson, L., Smoker, M., Perkins, S., and Foster, S. (2014). Elevating crop disease resistance with cloned genes. *Philos. Trans. R. Soc. B Biol. Sci.* 369: 20130087-20130087.

Jones, J. D. G., Vance, R. E., and Dangl, J. L. (2016). Intracellular innate immune surveillance devices in plants and animals. *Science* (80-.). 354:aaf6395.

Krasileva, K. V., Dahlbeck, D., and Staskawicz, B. J. (2010). Activation of an *Arabidopsis* Resistance Protein Is Specified by the in Planta Association of Its Leucine-Rich Repeat Domain with the Cognate Oomycete Effector. *Plant Cell* 22:2444-2458.

Li, W., Yadeta, K. A., Elmore, J. M., and Coaker, G. (2013a). The *Pseudomonas syringae* effector HopQ1 promotes bacterial virulence and interacts with tomato 14-3-3 proteins in a phosphorylation-dependent manner. *Plant Physiol.* 161:2062-74.

Li, W., Chiang, Y. H., and Coaker, G. (2013b). The HopQ1 Effector's Nucleoside Hydrolase-Like Domain Is Required for Bacterial Virulence in *Arabidopsis* and Tomato, but Not Host Recognition in Tobacco. *PLoS One* 8:1-9.

Lindgren, P. B., Peet, R. C., and Panopoulos, N. J. (1986). Gene cluster of *Pseudomonas syringae* pv. "*phaseolicola*" controls pathogenicity of bean plants and hypersensitivity of nonhost plants. *J. Bacteriol.* 168:512-522.

Liu, Y., Schiff, M., Marathe, R., and Dinesh-Kumar, S. P. (2002). Tobacco Rar1, EDS1 and NPR1/NIM1 like genes are required for N-mediated resistance to tobacco mosaic virus. *Plant J.* 30:415-429.

Marillonnet, S., Thoeringer, C., Kandzia, R., Klimyuk, V., and Gleba, Y. (2005). Systemic *Agrobacterium tumefaciens*-mediated transfection of viral replicons for efficient transient expression in plants. *Nat. Biotechnol.* 23:718-23.

Nakasugi, K., Crowhurst, R. N., Bally, J., Wood, C. C., Hellens, R. P., and Waterhouse, P. M. (2013). De Novo Transcriptome Sequence Assembly and Analysis of RNA Silencing Genes of *Nicotiana benthamiana*. *PLoS One* 8:e59534.

Oerke, E.-C. (2005). Crop losses to pests. *J. Agric. Sci.* 144:31.

Oh, C.-S., Pedley, K. F., and Martin, G. B. (2010). Tomato 14-3-3 protein 7 positively regulates immunity-associated programmed cell death by enhancing protein abundance and signaling ability of MAPKKKα. *Plant Cell* 22:260-272.

Peart, J. R., Mestre, P., Lu, R., Malcuit, I., and Baulcombe, D. C. (2005). NRG1, a CC-NB-LRR protein, together with N, a TIR-NB-LRR protein, mediates resistance against tobacco mosaic virus. *Curr. Biol.* 15:968-973.

Qi, T., Schultink, A., Pham, J., Cho, M.-J., and Staskawicz, B. (2018). NRG1 is required for the function of the TIR-NLR immune receptors Roq1 and RPP1 in *Nicotiana benthamiana*. *Biorxiv* Advance Access published 2018, doi:10.1101/284471.

Rodriguez-Moreno, L., Song, Y., and Thomma, B. P. (2017). Transfer and engineering of immune receptors to improve recognition capacities in crops. *Curr. Opin. Plant Biol.* 38:42-49.

Rossier, O., Wengelnik, K., Hahn, K., and Bonas, U. (1999). The *Xanthomonas* Hrp type III system secretes proteins from plant and mammalian bacterial pathogens. *Pnas* 96:9368-9373.

Schwartz, A. R., Potnis, N., Timilsina, S., Wilson, M., Patane, J., Martins, J., Minsavage, G. V., Dahlbeck, D., Akhunova, A., Almeida, N., et al. (2015). Phylogenomics of *Xanthomonas* field strains infecting pepper and tomato reveals diversity in effector repertoires and identifies determinants of host specificity. *Front. Microbiol.* 6:535.

Shirasu, K. (2009). The HSP90-SGT1 chaperone complex for NLR immune sensors. *Annu. Rev. Plant Biol.* 60:139-164.

Sinha, D., Gupta, M. K., Patel, H. K., Ranjan, A., and Sonti, R. V. (2013). Cell Wall Degrading Enzyme Induced Rice Innate Immune Responses Are Suppressed by the Type 3 Secretion System Effectors XopN, XopQ, XopX and XopZ of *Xanthomonas oryzae* pv. *oryzae*. *PLoS One* 8:1-19.

Teper, D., Salomon, D., Sunitha, S., Kim, J. G., Mudgett, M. B., and Sessa, G. (2014). *Xanthomonas euvesicatoria* type III effector XopQ interacts with tomato and pepper 14-3-3 isoforms to suppress effector-triggered immunity. *Plant J.* 77:297-309.

Toruño, T. Y., Stergiopoulos, I., and Coaker, G. (2016). Plant-Pathogen Effectors: Cellular Probes Interfering with Plant Defenses in Spatial and Temporal Manners. *Annu. Rev. Phytopathol.* 54:419-441.

Vincelli, P. (2016). Genetic engineering and sustainable crop disease management: Opportunities for case-by-case decision-making *Sustain.* 8.

Wei, C.-F., Kvitko, B. H., Shimizu, R., Crabill, E., Alfano, J. R., Lin, N.-C., Martin, G. B., Huang, H.-C., and Collmer, A. (2007). A *Pseudomonas syringae* pv. *tomato* DC3000 mutant lacking the type III effector HopQ1-1 is able to cause disease in the model plant *Nicotiana benthamiana*. *Plant J.* 51:32-46.

Wiermer, M., Feys, B. J., and Parker, J. E. (2005). Plant immunity: The EDS1 regulatory node. *Curr. Opin. Plant Biol.* 8:383-389.

Wu, C.-H., Belhaj, K., Bozkurt, T. O., and Kamoun, S. (2016). The NLR helper protein NRC3 but not NRC1 is required for Pto-mediated cell death in *Nicotiana benthamiana*. *New Phytol.* 209:1344-1352.

Wulff, B. B. H., Horvath, D. M., and Ward, E. R. (2011). Improving immunity in crops: New tactics in an old game. *Curr. Opin. Plant Biol.* 14:468-476.

Yu, S., Hwang, I., and Rhee, S. (2014). The crystal structure of type III effector protein XopQ from *Xanthomonas oryzae* complexed with adenosine diphosphate ribose. *Proteins* 82:2910-4.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

That which is claimed is:

1. A transgenic plant comprising an exogenous polynucleotide encoding a polypeptide that is identical to SEQ ID NO: 1, wherein the plant is not a *Nicotiana* plant.

2. The transgenic plant of claim 1, wherein the exogenous polynucleotide is operably linked to a promoter.

3. The transgenic plant of claim 2, wherein the promoter is exogenous to the plant.

4. The transgenic plant of claim 2, wherein the promoter is endogenous to the plant.

5. A seed of a transgenic plant of claim 1, wherein the seed comprises the exogenous polynucleotide.

6. A population of at least 100 plants of claim 1, growing in a field.

7. A method for enhancing the resistance of a non-*Nicotiana* plant to at least one species of *Xanthomonas, Pseudomonas* and/or *Ralstonia*, comprising:

(a) introducing an exogenous polynucleotide encoding a polypeptide that is at least 90% identical to SEQ ID NO: 1 into a non-*Nicotiana* plant cell;

(b) regenerating a transgenic non-*Nicotiana* plant from the non-*Nicotiana* plant cell; and (c) selecting said transgenic non-*Nicotiana* plant or a progeny of the same that contains the exogenous polynucleotide for resistance to *Xanthomonas, Pseudomonas*, and/or *Ralstonia.*

8. The method of claim 7, wherein the amino acid sequence of the polypeptide is at least 95% identical to the amino acid sequence of SEQ ID NO:1.

9. The method of claim 7, further comprising collecting seed from said transgenic non-*Nicotiana* plant or a progeny of the same that contains the exogenous polynucleotide.

* * * * *

SEQUENCE LISTING

<160> NUMBER OF SEQ ID NOS: 7

<210> SEQ ID NO 1
<211> LENGTH: 1306
<212> TYPE: PRT
<213> ORGANISM: Nicotiana benthamiana

<400> SEQUENCE: 1

```
Met Leu Thr Ser Ser His His Gly Arg Ser Tyr Asp Val Phe Leu
1               5                   10                  15

Ser Phe Arg Gly Glu Asp Thr Arg Lys Thr Phe Val Gly His Leu Phe
            20                  25                  30

Asn Ala Leu Ile Glu Lys Gly Ile His Thr Phe Met Asp Asp Lys Glu
            35                  40                  45

Leu Lys Arg Gly Lys Ser Ile Ser Ser Glu Leu Met Lys Ala Ile Gly
    50                  55                  60

Glu Ser Arg Phe Ala Val Val Val Phe Ser Lys Asn Tyr Ala Ser Ser
65                  70                  75                  80

Thr Trp Cys Leu Glu Glu Leu Val Lys Ile Leu Glu Ile His Glu Lys
                85                  90                  95

Phe Glu Leu Ile Val Val Pro Val Phe Tyr Asp Val Asp Pro Ser Thr
                100                 105                 110

Val Arg Lys Gln Asn Gly Glu Tyr Ala Val Cys Phe Thr Lys Phe Glu
            115                 120                 125

Ala Asn Leu Val Asp Asp Arg Asp Lys Val Leu Arg Trp Arg Glu Ala
        130                 135                 140

Leu Thr Lys Val Ala Asn Ile Ser Gly His Asp Leu Arg Asn Thr Tyr
145                 150                 155                 160

Asn Gly Asp Glu Ser Lys Cys Ile Gln Gln Ile Leu Lys Asp Ile Phe
                165                 170                 175

Asp Lys Phe Cys Phe Ser Ile Ser Ile Thr Asn Arg Asp Leu Val Gly
                180                 185                 190

Ile Glu Ser Gln Ile Lys Lys Leu Ser Ser Leu Leu Arg Met Asp Leu
            195                 200                 205

Lys Gly Val Arg Leu Val Gly Ile Trp Gly Met Gly Gly Val Gly Lys
    210                 215                 220

Thr Thr Ala Ala Arg Ala Leu Phe Asn Arg Tyr Tyr Gln Asn Phe Glu
225                 230                 235                 240

Ser Ala Cys Phe Leu Glu Asp Val Lys Glu Tyr Leu Gln His His Thr
                245                 250                 255

Leu Leu Tyr Leu Gln Lys Thr Leu Leu Ser Lys Leu Leu Lys Val Glu
                260                 265                 270

Phe Val Asp Cys Thr Asp Thr Glu Glu Met Cys Val Ile Leu Lys Arg
            275                 280                 285

Arg Leu Cys Ser Lys Lys Val Leu Val Val Leu Asp Asp Val Asn His
        290                 295                 300

Asn Asp Gln Leu Asp Lys Leu Val Gly Ala Glu Asp Trp Phe Gly Ser
305                 310                 315                 320

Gly Ser Arg Ile Val Ile Thr Thr Arg Asp Met Lys Leu Leu Lys Asn
                325                 330                 335

His Asp Val His Glu Thr Tyr Glu Ile Lys Val Leu Glu Lys Asp Glu
                340                 345                 350

Ala Ile Glu Leu Phe Asn Leu His Ala Phe Lys Arg Ser Ser Pro Glu
            355                 360                 365
```

```
Lys Glu Phe Lys Glu Leu Leu Asn Leu Val Val Asp Tyr Thr Gly Gly
    370                 375                 380

Leu Pro Leu Ala Leu Lys Val Leu Gly Ser Leu Leu Tyr Lys Glu Asp
385                 390                 395                 400

Leu Asp Val Trp Ile Ser Thr Ile Asp Arg Leu Lys Asp Asn Pro Glu
                405                 410                 415

Gly Glu Ile Met Ala Thr Leu Lys Ile Ser Phe Asp Gly Leu Arg Asp
            420                 425                 430

Tyr Glu Lys Ser Ile Phe Leu Asp Ile Ala Cys Phe Phe Arg Gly Tyr
        435                 440                 445

Asn Gln Arg Asp Met Thr Ala Leu Phe His Ala Ser Gly Phe His Pro
    450                 455                 460

Val Leu Gly Val Lys Thr Leu Val Glu Lys Ser Leu Ile Phe Ile Leu
465                 470                 475                 480

Glu Asp Lys Ile Gln Met His Asp Leu Met Gln Glu Met Gly Arg Gln
                485                 490                 495

Ile Ala Val Gln Glu Ser Pro Met Arg Arg Ile Tyr Arg Pro Glu Asp
            500                 505                 510

Val Lys Asp Ala Cys Ile Gly Asp Met Arg Lys Glu Ala Ile Glu Gly
        515                 520                 525

Leu Leu Leu Thr Glu Pro Glu Gln Phe Glu Gly Glu Leu Glu Tyr
    530                 535                 540

Met Tyr Ser Ala Glu Ala Leu Lys Lys Thr Arg Arg Leu Arg Ile Leu
545                 550                 555                 560

Val Lys Glu Tyr Tyr Asn Arg Gly Phe Asp Glu Pro Val Ala Tyr Leu
                565                 570                 575

Pro Asn Ser Leu Leu Trp Leu Glu Trp Arg Asn Tyr Ser Ser Asn Ser
            580                 585                 590

Phe Pro Ser Asn Phe Glu Pro Ser Lys Leu Val Tyr Leu Thr Met Lys
        595                 600                 605

Gly Ser Ser Ile Ile Glu Leu Trp Asn Gly Ala Lys Arg Leu Ala Phe
    610                 615                 620

Leu Thr Thr Leu Asp Leu Ser Tyr Cys His Lys Leu Ile Gln Thr Pro
625                 630                 635                 640

Asp Phe Arg Met Ile Thr Asn Leu Glu Arg Leu Ile Leu Ser Ser Cys
                645                 650                 655

Asp Ala Leu Val Glu Val His Pro Ser Val Gly Phe Leu Lys Asn Leu
            660                 665                 670

Ile Leu Leu Asn Met Asp His Cys Ile Ser Leu Glu Arg Leu Pro Ala
        675                 680                 685

Ile Ile Gln Ser Glu Cys Leu Glu Val Leu Asp Leu Asn Tyr Cys Phe
    690                 695                 700

Asn Leu Lys Met Phe Pro Glu Val Glu Arg Asn Met Thr His Leu Lys
705                 710                 715                 720

Lys Leu Asp Leu Thr Ser Thr Gly Ile Arg Glu Leu Pro Ala Ser Ile
                725                 730                 735

Glu His Leu Ser Ser Leu Glu Asn Leu Gln Met His Ser Cys Asn Gln
            740                 745                 750

Leu Val Ser Leu Pro Ser Ser Ile Trp Arg Phe Arg Asn Leu Lys Ile
        755                 760                 765

Ser Glu Cys Glu Lys Leu Gly Ser Leu Pro Glu Ile His Gly Asn Ser
    770                 775                 780
```

```
Asn Cys Thr Arg Glu Leu Ile Leu Lys Leu Val Ser Ile Lys Glu Leu
785                 790                 795                 800

Pro Thr Ser Ile Gly Asn Leu Thr Ser Leu Asn Phe Leu Glu Ile Cys
            805                 810                 815

Asn Cys Lys Thr Ile Ser Ser Leu Ser Ser Ser Ile Trp Gly Leu Thr
        820                 825                 830

Ser Leu Thr Thr Leu Lys Leu Leu Asp Cys Arg Lys Leu Lys Asn Leu
            835                 840                 845

Pro Gly Ile Pro Asn Ala Ile Asn His Leu Ser Gly His Gly Leu Gln
        850                 855                 860

Leu Leu Leu Thr Leu Glu Gln Pro Thr Ile Tyr Glu Arg Leu Asp Leu
865                 870                 875                 880

Leu Arg Ile Ile Asp Met Ser Trp Cys Ser Cys Ile Ser Ser Leu Pro
                885                 890                 895

His Asn Ile Trp Met Leu Lys Phe Leu Arg Ile Leu Cys Ile Ser Tyr
            900                 905                 910

Cys Ser Arg Leu Glu Tyr Leu Pro Glu Asn Leu Gly His Leu Glu His
        915                 920                 925

Leu Glu Glu Leu Leu Ala Asp Gly Thr Gly Ile Leu Arg Leu Pro Ser
930                 935                 940

Ser Val Ala Arg Leu Asn Lys Leu Glu Val Leu Ser Phe Arg Lys Lys
945                 950                 955                 960

Phe Ala Ile Gly Pro Lys Val Gln Tyr Ser Ser Ser Met Leu Asn Leu
            965                 970                 975

Pro Asp Asp Val Phe Gly Ser Leu Gly Ser Leu Gly Ser Val Val Lys
        980                 985                 990

Leu Asn Leu Ser Gly Asn Gly Phe Cys Asn Leu Pro Glu Thr Met Asn
        995                 1000                1005

Gln Leu Phe Cys Leu Glu Tyr Leu Asp Ile Thr Phe Cys Gln Arg
    1010                1015                1020

Leu Glu Ala Leu Pro Glu Leu Pro Pro Ser Ile Lys Glu Leu Tyr
    1025                1030                1035

Val Asp Glu His Leu Ala Leu Arg Ile Met Glu Asp Leu Val Ile
    1040                1045                1050

Lys Cys Lys Glu Leu Asn Leu Ile Ala Val Thr Lys Ile Glu Tyr
    1055                1060                1065

Gln Asn Phe Tyr Arg Trp Leu Asp Ser Ile Trp Ser Asp Val Ser
    1070                1075                1080

Glu Leu Leu Glu Asn Ser Gln Lys Gln Gln Leu Asp Asp Met Leu
    1085                1090                1095

Gln Leu Ile Pro Phe Ser Tyr Leu Ser Thr Ala Lys Arg Glu Glu
    1100                1105                1110

Val Leu Lys Ile Val Ile His Gly Thr Arg Ile Pro Glu Trp Phe
    1115                1120                1125

Arg Trp Gln Asp Arg Ser Ala Thr Thr Met Ser Val Asn Leu Pro
    1130                1135                1140

Glu Tyr Trp Tyr Thr Glu Asn Phe Leu Gly Phe Ala Ile Cys Cys
    1145                1150                1155

Ser Cys Cys Phe Tyr His Ser Ala Arg Ser Tyr Asp Val Glu Phe
    1160                1165                1170

Glu Gly Ser Met His His Tyr Asn Tyr Asp Ser Ser Tyr Trp Lys
    1175                1180                1185
```

```
Glu Tyr Glu Glu Pro Ser Tyr Asp Phe Tyr Glu Arg Asp Ser Ile
    1190                1195                1200

Glu Ile Thr Ala Lys Leu Thr Pro Arg His Lys Gly Met Arg Thr
    1205                1210                1215

Glu Glu Leu Lys Lys Val Cys Ser Phe Ser Met Asn Val Leu Arg
    1220                1225                1230

Arg Ala Thr Ala Val Pro Asn Met Cys Phe Ala Phe Phe Pro Phe
    1235                1240                1245

Asn Ser Leu Cys His Ile Ser Asn Leu Gln Ala Asn Asn Pro Asn
    1250                1255                1260

Asp Tyr Gly Ile Phe Glu Thr Cys Leu Ser Pro Gly Asp Ile Arg
    1265                1270                1275

His Arg Gly Lys Gln Trp Gly Phe Asn Leu Val Tyr Lys Asp Glu
    1280                1285                1290

Thr Gly Gly Ser Val Thr His Glu Met Leu Ile Asn Arg
    1295                1300                1305

<210> SEQ ID NO 2
<211> LENGTH: 45
<212> TYPE: PRT
<213> ORGANISM: Nicotiana benthamiana

<400> SEQUENCE: 2

Leu Lys Ile Ser Phe Asp Gly Leu Arg Asp Tyr Glu Lys Ser Ile Phe
1               5                   10                  15

Leu Asp Ile Ala Cys Phe Phe Arg Gly Tyr Asn Gln Arg Asp Met Thr
            20                  25                  30

Ala Leu Phe His Ala Ser Gly Phe His Pro Val Leu Gly
        35                  40                  45

<210> SEQ ID NO 3
<211> LENGTH: 45
<212> TYPE: PRT
<213> ORGANISM: Nicotiana tabacum

<400> SEQUENCE: 3

Leu Lys Ile Ser Phe Asp Gly Leu Arg Tyr Tyr Glu Lys Ser Ile Phe
1               5                   10                  15

Leu Asp Ile Ala Cys Phe Phe Arg Gly Tyr Asn Gln Arg Asp Met Thr
            20                  25                  30

Ala Leu Phe His Ala Ser Gly Phe His Pro Val Leu Gly
        35                  40                  45

<210> SEQ ID NO 4
<211> LENGTH: 4
<212> TYPE: PRT
<213> ORGANISM: Nicotiana sylvestris

<400> SEQUENCE: 4

Gln Ser Thr Lys
1

<210> SEQ ID NO 5
<211> LENGTH: 4
<212> TYPE: PRT
<213> ORGANISM: Nicotiana sylvestris

<400> SEQUENCE: 5

Thr Ser Ile Ile
1
```

-continued

```
<210> SEQ ID NO 6
<211> LENGTH: 17
<212> TYPE: PRT
<213> ORGANISM: Nicotiana sylvestris

<400> SEQUENCE: 6

Tyr Ile Tyr Asn Ile Phe Leu Asp Ile Ala Cys Phe Phe Arg Gly Tyr
1               5                   10                  15

Asn

<210> SEQ ID NO 7
<211> LENGTH: 17
<212> TYPE: PRT
<213> ORGANISM: Nicotiana sylvestris

<400> SEQUENCE: 7

Arg Asp Met Thr Ala Leu Phe His Ala Ser Gly Phe His Pro Val Leu
1               5                   10                  15

Gly
```